United States Patent
Cheaz et al.

(10) Patent No.: US 12,272,450 B2
(45) Date of Patent: Apr. 8, 2025

(54) REVERSE RECALL NOTIFICATION SYSTEM

(71) Applicant: INTERNATIONAL BUSINESS MACHINES CORPORATION

(72) Inventors: Nixon Cheaz, Cary, NC (US); Vince Siu, Thornhill (CA); Clayton M. Billups, Cary, NC (US); Jian Zhang, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 176 days.

(21) Appl. No.: 17/448,588

(22) Filed: Sep. 23, 2021

(65) Prior Publication Data

US 2023/0092553 A1    Mar. 23, 2023

(51) Int. Cl.
G16H 40/40      (2018.01)
H04L 67/12      (2022.01)

(52) U.S. Cl.
CPC ............ G16H 40/40 (2018.01); H04L 67/12 (2013.01)

(58) Field of Classification Search
CPC ................................ G16H 40/40; H04L 67/12
See application file for complete search history.

(56) References Cited

U.S. PATENT DOCUMENTS

| | | | |
|---|---|---|---|
| 10,734,119 B2 | 8/2020 | Kozloski | |
| 2001/0056359 A1 | 12/2001 | Abreu | |
| 2006/0287689 A1 | 12/2006 | Debruyne | |
| 2007/0255339 A1* | 11/2007 | Torgerson | A61N 1/0529 607/45 |
| 2010/0222846 A1* | 9/2010 | Goetz | G16H 40/40 607/59 |
| 2012/0112903 A1 | 5/2012 | Kaib | |
| 2014/0249838 A1 | 9/2014 | Gelb | |
| 2014/0288943 A1* | 9/2014 | Kaniyur-Subbian | G16Z 99/00 705/2 |
| 2015/0234995 A1* | 8/2015 | Casady | G06Q 10/087 705/2 |

(Continued)

FOREIGN PATENT DOCUMENTS

WO     2001049368 A1     7/2001

OTHER PUBLICATIONS

Wilson NA, Reich AJ, Graham J, Bhatt DL, Nguyen LL, Weissman JS. Patient perspectives on the need for implanted device information: Implications for a post-procedural communication framework. Health Expect. Aug. 2021;24(4):1391-1402. doi: 10.1111/hex. 13273. (Year: 2021).*

(Continued)

*Primary Examiner* — Fonya M Long
*Assistant Examiner* — Patricia K. Edouard
(74) *Attorney, Agent, or Firm* — Kimberly Zillig

(57) ABSTRACT

Aspects of this disclosure include a recall notification method, a method for communicating an action to be performed by a device, and a method of operating a relay service by a network device. One embodiment of the recall notification method may comprise periodically transmitting, by a network interface of a medical device implanted in a user's body, a poll request to a recall service endpoint. The method may further comprise receiving, by the network interface in response to the poll request, a recall notification; and in response to receiving the recall notification, directly notifying the user.

9 Claims, 8 Drawing Sheets

(56) References Cited

U.S. PATENT DOCUMENTS

| | | | |
|---|---|---|---|
| 2016/0038749 A1* | 2/2016 | Maile | A61N 1/37252 607/31 |
| 2016/0189321 A1* | 6/2016 | Halpern | G16H 80/00 705/2 |
| 2016/0250486 A1* | 9/2016 | Yoder | G16Z 99/00 340/870.07 |
| 2016/0306929 A1 | 10/2016 | Butka | |
| 2018/0351987 A1 | 12/2018 | Patel | |
| 2019/0158353 A1* | 5/2019 | Johnson | H04L 41/0803 |
| 2019/0189274 A1 | 6/2019 | Kalia | |
| 2019/0214150 A1* | 7/2019 | Kozloski | G16H 40/67 |
| 2021/0265045 A1* | 8/2021 | Elias | G16H 30/20 |
| 2021/0313076 A1* | 10/2021 | Jho | G16H 80/00 |
| 2022/0168065 A1* | 6/2022 | McNutt | A61B 90/98 |

OTHER PUBLICATIONS

Nakayama M, Tanaka S, Hamada S, Uchida T, Kawakami K. Recalls and Premarket Review Systems for High-Risk Medical Devices in Japan. Therapeutic Innovation & Regulatory Science. 2019;53(6):775-780. doi: 10.1177/2168479018812812 (Year: 2019).*

"Pacemakers." NIH, U.S. Department of Health Human Services, www.nhlbi.nih.gov/health-topics/pacemakers. Retrieved from internet on Aug. 20, 2021.

Burri H, Senouf D. Remote monitoring and follow-up of pacemakers and implantable cardioverter defibrillators [published correction appears in Europace. Nov. 2009; 11(11):1569]. Europace. 2009;11(6):701-709. doi: 10.1093/europace/eup110.

Disclosed Anonymously, "Intentionally Causing Controlled Wounds/Discomfort to Alert Implant Device Recipients of Highly Critical Failure Events," IP.com No. IPCOM000266043D, IP.com Electronic Publication Date: Jun. 8, 2021, https://priorart.ip.com/IPCOM/000266043.

Ghaly, Ramsis F et al. "Do we need to establish guidelines for patients with neuromodulation implantable devices, Including spinal cord stimulators undergoing nonspinal surgeries ?. " Surgical neurology international vol. 7 18. Feb. 15, 2016, doi: 10.4103/2152-7806.176373.

Jetter, Alexis. "Medical Implants May Be Hazardous to Your Health." GH, Feb. 10, 2004, www.goodhousekeeping.com/health/a1556/medical-implants-hazardous-health-feb04/. Retrieved from internet on Aug. 18, 2021.

Landolina, Maurizio et al, "Remote Monitoring Reduces Healthcare Use and Improves Quality of Care in Heart Failure Patients With Implantable Defibrillators," Circulation, Jun. 19, 2012, vol. 125, Issue 24, pp. 2985-2992, https://www.ahajournals.org/doi/full/10.1161/CIRCULATIONAHA.111.088971.

Product and Service Information Updates. www.medtronicdiabetes.com/customer-support/product-and-service-updates. Retrieved from internet on Aug. 20, 2021.

Siarri, Danielle. "A Medical Device Recall Workflow Is an Underrated Thing." Medium, Jul. 20, 2019, medium.com/nuadox/a-medical-device-recall-workflow-is-an-underrated-thing-3da1a2771ec1. Retrieved from the internet on Aug. 18, 2021.

* cited by examiner

REVERSE RECALL NOTIFICATION SYSTEM

The following disclosure(s) are submitted under 35 U.S.C. 102(b)(1)(A): "Intentionally Causing Controlled Wounds/Discomfort to Alert Implant Device Recipients of Highly Critical Failure Events," anonymously published by Nixon Cheaz, Vince Siu, Clayton M. Billups, Jian Zhang on 2021 Jun. 8 at https://priorart.ip.com/IPCOM/00466043D.

BACKGROUND

The present disclosure relates to notification systems, and more specifically, to a reverse recall notification system.

The development of the EDVAC system in 1948 is often cited as the beginning of the computer era. Since that time, computer systems have evolved into extremely complicated devices. Today's computer systems typically include a combination of sophisticated hardware and software components, application programs, operating systems, processors, buses, memory, input/output devices, and so on. As advances in semiconductor processing and computer architecture push performance higher and higher, even more advanced computer software has evolved to take advantage of the higher performance of those capabilities, resulting in computer systems today that are much more powerful than just a few years ago.

One application of these capabilities is the implantable medical device. An estimated twenty-five million Americans, plus many more worldwide, rely on such devices for their health and wellbeing. Although these devices are rigorously tested, problems and issues can still occur after they have been implanted in a patient. Some of these problems and issues may pose significant health risks to the patient.

SUMMARY

According to embodiments of the present disclosure, a recall notification method, comprising periodically transmitting, by a network interface of a medical device implanted in a user's body, a poll request to a recall service endpoint. The method may further comprise receiving, by the network interface in response to the poll request, a recall notification; and in response to receiving the recall notification, directly notifying the user.

According to embodiments of the present disclosure, a method for communicating an action to be performed by a device, comprising providing an Internet of things (IoT) interface for communicating with a plurality of devices, and receiving, by the IoT interface, communications from the plurality of devices. The communications may comprise device identification information from the plurality of devices. The method may further comprise analyzing the communications from the plurality of devices to determine a customized processing action for each of the plurality of devices, and returning, by the IoT interface to the devices, the customized processing action. The plurality of devices comprise medical devices implanted in a patient.

According to embodiments of the present disclosure, a method of operating a relay service by a network device, comprising providing an Internet of things (IoT) interface for communicating with a plurality of devices, and receiving, by the IoT interface, communications from one of the plurality of devices. The method may further comprise determining, by a processor, that the communication comprises an anonymous status request, and in response to the determination, automatically relaying the anonymous status request to a status service. The plurality of devices may comprise implanted medical devices.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
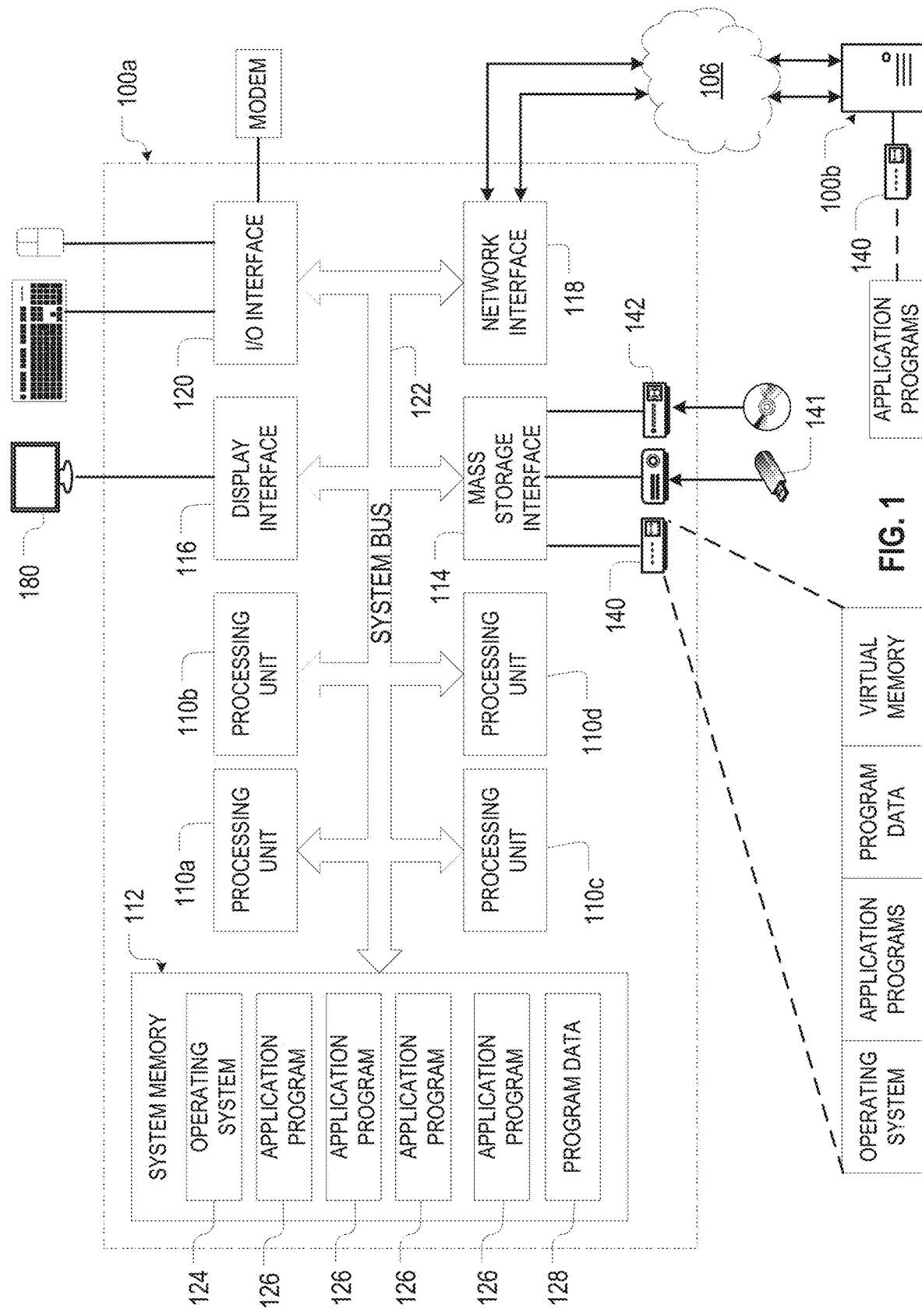
FIG. 1 illustrates one embodiment of a data processing system (DPS), consistent with some embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to notification systems; more particular aspects relate to a reverse recall notification system. While the present disclosure is not necessarily limited to such applications, various aspects of the disclosure may be appreciated through a discussion of various examples using this context.

Implantable medical devices greatly improve the health and well-being of many patients. Between 1990 and 2001, however, 689 recall notices affecting more than two million implanted devices were issued. Currently, patients are informed about these recalls in a manner similar to other consumer products. More specifically, the manufacturer of the implantable medical device maintains a database of customers. In the event of a recall, e-mails, letters, and/or direct telephone calls are made to the patients' physicians-of-record, as listed in that database. Those physicians, in turn, try to locate and contact the actual patients in which the devices are implanted. This process, however, has numerous potential points of failure, particularly as these devices may have long service lives. For example, in years/decades after a device was implanted, the physician-of-record may have retired, or the patient may have moved and/or changed their contact information (e.g., phone numbers and email addresses), or may currently live in an area that lacks high quality public services. This recall process also does not take into account the higher risk that recalls on an implanted medical device may represent as compared to other types of consumer products, both in terms of human health and potential liability for the manufacturer.

An attempt at modernizing the recall process relies on each physician scanning a bar code on the device using a mobile application, and then correctly linking that image to a patient record. This information is stored in a central database, which is used to contact patients in the event of a recall. This system, however, still requires that the information in the central database be accurate/maintained over long periods of time, often decades. That is, this modernized system cannot ensure that all affected patients will get reliably and uniformly notified in the case of a recall, regardless of how long ago the patient received the implanted device; how many times the patient has switched doctors; whether or not patient have changed names, phone numbers, moved outside the country; regardless of whether the physician is still alive and/or in business, etc.

Accordingly, one aspect of some embodiments is an implanted medical device (i.e., in a user/patient) that that is able to periodically contact the device manufacturer and/or a recall service via radio frequency (RF) data transfer, such as cellular, Wi-Fi, and Bluetooth. The implanted device in some embodiments may then determine whether or not any recall notices have been issued for it. If a recall has been issued, the implanted device may then interact directly with its user in some embodiments. Additionally or alternatively, the implanted device in some of these embodiments may periodically execute self-diagnosis routine, conclude that there is a need for the patient to seek immediate medical attention, and then interact directly with its user.

If the recall notice and/or error code indicates that immediate medical attention is needed, then the implanted device in some embodiments may directly alert its user by generating a mild tactile sensation (i.e., something the user can feel). In some embodiments, this mild tactile sensation may be generated at an intensity low enough to safely alert the recipient that immediate attention is needed, but without causing harm or significant pain. In this way, some embodiments may mimic the way natural feelings of discomfort alert a person that something happening in the person's body needs attention. Accordingly, one feature and advantage of some embodiments utilizing tactile sensation is that they may interact directly with the patient/user to alert that patient/user of important or even critical emergency events (e.g., something is critically wrong with the implanted device that must be addressed as soon as possible) without requiring that any external and/or third party systems have their correct current contact information.

Another aspect of some embodiments is a reverse recall notification method that may help ensure that all of the products' users get notified of the recall, and which may reduce or even eliminate the need for manual actions. This reverse recall method may be particularly desirable for use in implanted medical devices because such devices are often difficult to inspect/access and because the user/patient may often move many times during the device's lifecycle. Devices using this reverse recall notification method may include a RF network interface, such as devices that use one or more of the cellular, 802.1X (WIFI), and Bluetooth protocols. The device may periodically poll an internet data endpoint associated with the manufacturer and/or a recall service for recall notices and/or recall information about itself. The address of this data endpoint may be fixed, and may be programmed into the device by the manufacturer during the manufacturing process. In this way, some embodiments may receive data directly from a device manufacturer and/or a recall service, which may include the recall notification.

Most of the periodic polls may return a negative result (i.e., a code indicating that no recall has been issued for that device) in some embodiments. However, in the event that there was a recall issued, the periodic poll will return a positive result (i.e., a code indicating that a recall has been issued and that the patient should seek immediate medical assistance). This positive result code may be encrypted for each specific device (e.g., exclusive-OR with an embedded serial number for the device) in some embodiments. Additionally or alternatively, this positive result code may be cryptographically signed by the manufacturer of the device and/or by the recall service.

Once the device finds out there is a recall and/or its internal self-diagnosis routines indicate that there is an error, the device may proceed to directly notify its user. In embodiments implemented in implanted medical devices, this direct notification may include generating a tactile sensation (e.g., mild pressure and/or discomfort) in the patient/user. When the patient/user receives the tactile sensation, the patient/user will instinctively go to a doctor to "get checked." The physician, in turn, may contact the manufacturer to confirm that a recall has been issued and/or may perform a diagnostic on the implanted device that will reveal that there is a recall on the device. In this way, the tactile notification system of some embodiments may enable direct notification of a recall to the patient/user even if nobody (e.g., the implanted device, the device manufacturer, the doctor of record, etc.) has the patient/user's current contact information (e.g., current phone number, e-mail address, etc.)

In the event that the patient/user recognizes that a tactile notification is occurring, but is not, at the moment, in a position to resolve it, some embodiments may include a manual override. For example, some embodiments may allow a user to download a special mobile application that can interact with the implanted device and switch off the tactile sensation. Other embodiments may allow the user to switch off the tactile sensation using e.g., a particular series of movements or a targeted magnetic field.

Accordingly, one feature and advantage of the reverse recall notification method in some embodiments is that they may enable near complete (100%) notification because the device may communicate directly with a recall endpoint, and then may notify the patient/user directly (e.g., via tactile sensation). This novel recall notification method not only works more reliably, but may also work without the need for any record keeping and/or updates to records of any kind. The system/device using this reverse recall notification method may always be able to get the relevant recall information from the correct recall endpoint, and then may notify the user directly, all without any record keeping and/or any updater of such records. All affected patients may get reliably and uniformly notified, regardless of how long ago they took the implanted device, how many times that patient has switched doctors, changed names, changed phone numbers, moved outside the country, etc., as long as they occasionally pass through an area with wireless connectivity.

Another feature and advantage of some embodiments is that they may eliminate the need for human action (and thus, human error) to communicate the recall notification to the patient. That is, when a recall is issued, there is no longer need for the manufacture to send e-mails, making telephone calls, mail letters to the user/patient and/or the patient's doctor to communicate the recall. This, in turn, may reduce or eliminate the dependency on a central registry of patients that needs to be manually maintained over decades, and may ultimately still be unreliable when needed.

Another feature and advantage of some embodiments is that there is no need to involve a primary care physician or other middleman in the recall notification process. The user/patient may be made directly aware that something is wrong with the device, and in response, they will naturally desire to "get it checked." This feature and advantage may also reduce or eliminate the delays and errors associated with any system that relies on such intermediate parties. Another feature and advantage of some embodiments is that there is no need for the doctor or patient to setup and configure an application on a smartphone prior to implanting the device, or to keep such app's information updated as situations change. Similarly, some embodiment may reduce the opportunity for errors that could result from incorrectly using such an application.

FIG. 1 illustrates one embodiment of a data processing system (DPS) 100a, 100b (herein generically referred to as a DPS 100), consistent with some embodiments. FIG. 1 only depicts the representative major components of the DPS 100, and those individual components may have greater complexity than represented in FIG. 1. In some embodiments, the DPS 100 may be implemented as a personal computer; server computer; portable computer, such as a laptop or notebook computer, PDA (Personal Digital Assistant), tablet computer, or smartphone; processors embedded into larger devices, such as an automobile, airplane, teleconferencing system, appliance; smart devices; or any other appropriate type of electronic device. Moreover, components other than or in addition to those shown in FIG. 1 may be present, and that the number, type, and configuration of such components may vary.

The data processing system 100 in FIG. 1 may comprise a plurality of processing units 110a-110d (generically, processor 110 or CPU 110) that may be connected to a main memory 112, a mass storage interface 114, a terminal/display interface 116, a network interface 118, and an input/output ("I/O") interface 120 by a system bus 122. The mass storage interfaces 114 in this embodiment may connect the system bus 122 to one or more mass storage devices, such as a direct access storage device 140, a USB drive 141, and/or a readable/writable optical disk drive 142. The one or more direct access storage devices 140 may be logically organized into a RAID array, which in turn, may be managed by a RAID controller 115 in e.g., the mass storage interface 114, by software executing on the processor 110, or a combination of both. The network interfaces 118 may allow the DPS 100a to communicate with other DPS 100b over a network 106. The main memory 112 may contain an operating system 124, a plurality of application programs 126, and program data 128.

The DPS 100 embodiment in FIG. 1 may be a general-purpose computing device. In these embodiments, the processors 110 may be any device capable of executing program instructions stored in the main memory 112, and may themselves be constructed from one or more microprocessors and/or integrated circuits. In some embodiments, the DPS 100 may contain multiple processors and/or processing cores, as is typical of larger, more capable computer systems; however, in other embodiments, the computing systems 100 may only comprise a single processor system and/or a single processor designed to emulate a multiprocessor system. Further, the processor(s) 110 may be implemented using a number of heterogeneous data processing systems 100 in which a main processor 110 is present with secondary processors on a single chip. As another illustrative example, the processor(s) 110 may be a symmetric multiprocessor system containing multiple processors 110 of the same type.

When the DPS 100 starts up, the associated processor(s) 110 may initially execute program instructions that make up the operating system 124. The operating system 124, in turn, may manage the physical and logical resources of the DPS 100. These resources may include the main memory 112, the mass storage interface 114, the terminal/display interface 116, the network interface 118, and the system bus 122. As with the processor(s) 110, some DPS 100 embodiments may utilize multiple system interfaces 114, 116, 118, 120, and buses 122, which in turn, may each include their own separate, fully programmed microprocessors.

Instructions for the operating system 124 and/or application programs 126 (generically, "program code," "computer usable program code," or "computer readable program code") may be initially located in the mass storage devices, which are in communication with the processor(s) 110 through the system bus 122. The program code in the different embodiments may be embodied on different physical or tangible computer-readable media, such as the memory 112 or the mass storage devices. In the illustrative example in FIG. 1, the instructions may be stored in a functional form of persistent storage on the direct access storage device 140. These instructions may then be loaded into the main memory 112 for execution by the processor(s) 110. However, the program code may also be located in a functional form on the computer-readable media, such as the direct access storage device 140 or the readable/writable optical disk drive 142, that is selectively removable in some embodiments. It may be loaded onto or transferred to the DPS 100 for execution by the processor(s) 110.

With continuing reference to FIG. 1, the system bus 122 may be any device that facilitates communication between and among the processor(s) 110; the main memory 112; and the interface(s) 114, 116, 118, 120. Moreover, although the system bus 122 in this embodiment is a relatively simple, single bus structure that provides a direct communication path among the system bus 122, other bus structures are consistent with the present disclosure, including without limitation, point-to-point links in hierarchical, star or web configurations, multiple hierarchical buses, parallel and redundant paths, etc.

The main memory 112 and the mass storage device(s) 140 may work cooperatively to store the operating system 124, the application programs 126, and the program data 128. In some embodiments, the main memory 112 may be a random-access semiconductor memory device ("RAM") capable of storing data and program instructions. Although FIG. 1 conceptually depicts that the main memory 112 as a single monolithic entity, the main memory 112 in some embodiments may be a more complex arrangement, such as a hierarchy of caches and other memory devices. For example, the main memory 112 may exist in multiple levels of caches, and these caches may be further divided by function, such that one cache holds instructions while another cache holds non-instruction data that is used by the processor(s) 110. The main memory 112 may be further distributed and associated with a different processor(s) 110 or sets of the processor(s) 110, as is known in any of various so-called non-uniform memory access (NUMA) computer architectures. Moreover, some embodiments may utilize virtual addressing mechanisms that allow the DPS 100 to behave as if it has access to a large, single storage entity instead of access to multiple, smaller storage entities (such as the main memory 112 and the mass storage device 140).

Although the operating system 124, the application programs 126, and the program data 128 are illustrated in FIG. 1 as being contained within the main memory 112 of DPS 100a, some or all of them may be physically located on a different computer system (e.g., DPS 100b) and may be accessed remotely, e.g., via the network 106, in some embodiments. Moreover, the operating system 124, the application programs 126, and the program data 128 are not necessarily all completely contained in the same physical DPS 100a at the same time, and may even reside in the physical or virtual memory of other DPS 100b.

The system interfaces 114, 116, 118, 120 in some embodiments may support communication with a variety of storage and I/O devices. The mass storage interface 114 may support the attachment of one or more mass storage devices 140, which may include rotating magnetic disk drive storage devices, solid-state storage devices (SSD) that uses integrated circuit assemblies as memory to store data persistently, typically using flash memory or a combination of the two. Additionally, the mass storage devices 140 may also comprise other devices and assemblies, including arrays of disk drives configured to appear as a single large storage device to a host (commonly called RAID arrays) and/or archival storage media, such as hard disk drives, tape (e.g., mini-DV), writable compact disks (e.g., CD-R and CD-RW), digital versatile disks (e.g., DVD, DVD-R, DVD+R, DVD+RW, DVD-RAM), holography storage systems, blue laser disks, IBM Millipede devices, and the like. The I/O interface 120 may support attachment of one or more I/O devices, such as a keyboard 181, mouse 182, modem 183, or printer (not shown)

The terminal/display interface 116 may be used to directly connect one or more displays 180 to the data processing system 100. These displays 180 may be non-intelligent (i.e., dumb) terminals, such as an LED monitor, or may themselves be fully programmable workstations that allow IT administrators and users to communicate with the DPS 100. Note, however, that while the display interface 116 may be provided to support communication with one or more displays 180, the computer systems 100 does not necessarily require a display 180 because all needed interaction with users and other processes may occur via the network 106.

The network 106 may be any suitable network or combination of networks and may support any appropriate protocol suitable for communication of data and/or code to/from multiple DPS 100. Accordingly, the network interfaces 118 may be any device that facilitates such communication, regardless of whether the network connection is made using present-day analog and/or digital techniques or via some networking mechanism of the future. Suitable networks 106 include, but are not limited to, networks implemented using one or more of the "InfiniBand" or IEEE (Institute of Electrical and Electronics Engineers) 802.3x "Ethernet" specifications; cellular transmission networks; wireless networks implemented one of the IEEE 802.11x, IEEE 802.16, General Packet Radio Service ("GPRS"), FRS (Family Radio Service), or Bluetooth specifications; Ultra-Wide Band ("UWB") technology, such as that described in FCC 02-48; or the like. Those skilled in the art will appreciate that many different network and transport protocols may be used to implement the network 106. The Transmission Control Protocol/Internet Protocol ("TCP/IP") suite contains a suitable network and transport protocols.

Figure 2:
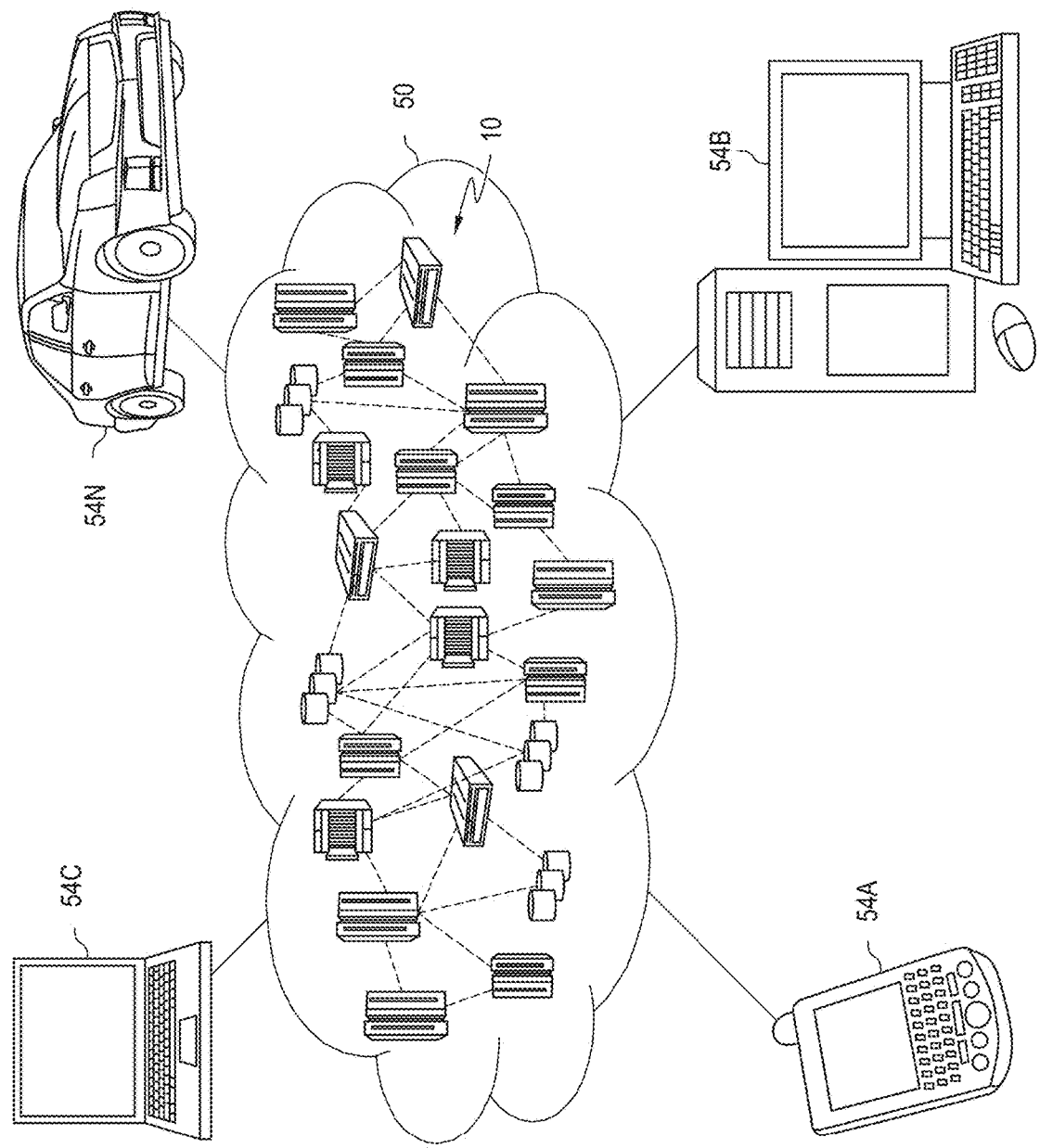
FIG. 2 illustrates one embodiment of a cloud environment, consistent with some embodiments.

FIG. 2 illustrates one embodiment of a cloud environment suitable for an edge enabled scalable and dynamic transfer learning mechanism. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
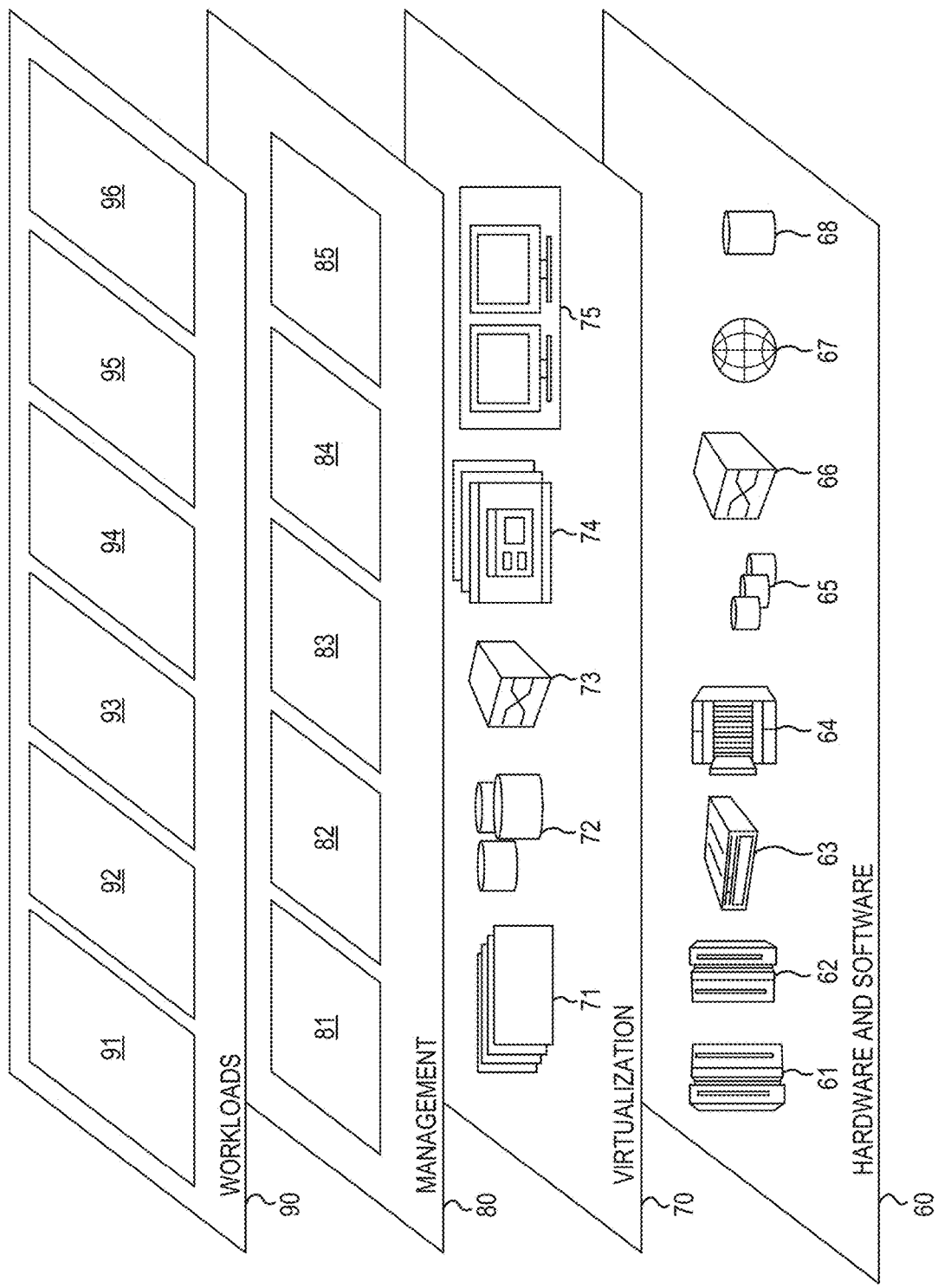
FIG. 3 shows a set of functional abstraction layers, consistent with some embodiments.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and recall service 96. This recall service 96 may be operated by an implantable device manufacturer, or may be operated by a recall service that serves as a central repository for all recalls by a plurality of different manufacturers.

Figure 4:
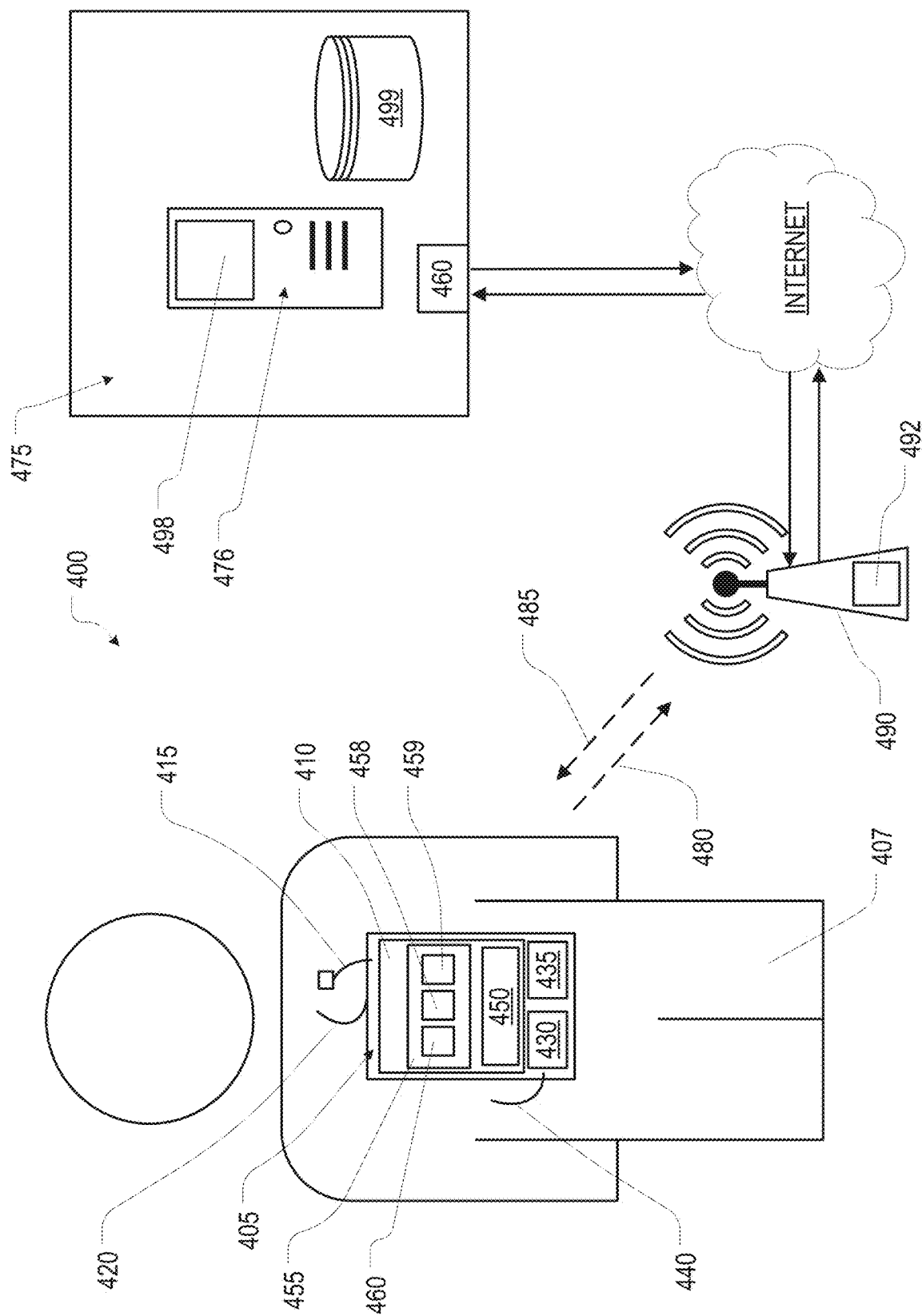
FIG. 4 is a diagram illustrating a reverse recall system, consistent with some embodiments.

FIG. 4 is a diagram illustrating a reverse recall system 400, consistent with some embodiments. An implanted medical device 405 (shown larger for clarity) in this embodiment may be implanted in a user's body 407 and may comprise a controller 410, one or more primary leads 415 that serve as inputs for the primary medical function (e.g., for a pacemaker, the patient's heartbeat) and one or more primary electrodes 420 that preform the primary medical function (e.g., for a pacemaker, the measured heartbeat is slower than normal, the primary electrodes 420 may deliver electrical impulses to their heart to cause it to beat normally). The implanted medical device 405 in this embodiment may also comprise a power source 430, a wireless network interface 435, and one or more secondary electrodes 440.

The controller 410 in some embodiments may include a recall polling module 450 and a nonvolatile memory 455. The nonvolatile memory 455 may contain an address 460 (e.g., an internet address) for a data endpoint 470 associated with a recall service 475, such as recall service 96. The nonvolatile memory 455 may also contain a serial number 458 for the implanted device 405 and/or a public cryptographic key 459 associated with the recall service 475. The recall service 475, in turn, may maintain a server 476, such as DPS 100, at the address 460 that may respond to a poll request 480 from the device 405 with a reply message 485 containing a return code. The return code may indicate whether or not a recall of a particular implanted device 405 has been issued by the manufacturer. This return code may be encrypted using the serial number 458 and/or a cryptographic key 459, such that the implanted device 405 may be assured that the return code in the reply message 485 is authentic.

The controller 410 may include a processor and/or one or more integrated circuits adapted to perform the functions described herein. In some embodiments, the controller 410 may comprise electronic circuitry including, for example, an application specific integrated circuit (ASIC), programmable logic controller (PLC), or field-programmable gate arrays (FPGA), that perform some or all of the operations described herein. Functions to perform these operations may be programmed into the integrated circuits of a processor of the implanted medical device 405, or loaded from memory, storage device, or network or combinations thereof.

The wireless network interface 435 may be any device that can poll and exchange data with the data endpoint 470 via radio frequency (RF) data transfer, such as cellular, Wi-Fi, and Bluetooth. In some embodiments, this polling and data exchange may occur via one or more intermediate devices 490, such as a cellular tower and base station, a WIFI endpoint and router, a smartphone, or the like, and may be formatted pursuant to one or more Internet-of-Things (IoT) communication protocols. The intermediate devices 490 may include a relay module 492, which is adapted to receive specially encoded messages from the implanted device 405 and forward those messages to the data endpoint 470. The encoding, in turn, may be any system adapted to signal to the relay module 492 that the message should be forwarded, such as appearing on a predetermined logical port number or prefaced by a predetermined handshake code. Upon receiving the specially encoded messages (and otherwise of the proper format), the relay module 492 may automatically forward the messages (including the poll request 480) regardless of other authentication/authorization mechanisms rules it may otherwise use. That is, the messages forwarded by the relay module 492 may be anonymous in some embodiments.

The power source 430 may be a battery or other power storage system adapted to provide sufficient power to perform the primary medical purpose, to periodically poll and data exchange with the data endpoint 470, and to generate tactile sensations (if necessary), for an extended period of time, such as several years. The one or more secondary electrodes 440 may be may any device or system capable of generating a tactile sensation in the user. In some embodiments, the secondary electrodes 440 may directly simulate a nerve or muscle in the user. In other embodiments, the secondary electrodes 440 may activate a biocompatible blister pack or other refillable container containing, e.g., saline solution, which may be located either on or in the device 405. The saline solution, in turn, may travel to a biocompatible inflatable cushion implanted subdermally, thereby causing a sensation of pressure. In other embodiments, the secondary electrodes 440 may activate an eccentric mass vibration motor to create a vibration. In some embodiment, the sensation generated by the secondary electrodes 440 may be proportional to a severity level of the recall, e.g., a mild sensation for recalls that only affect quality of live and a more intense sensation for recalls that are potentially life threatening.

Figure 5A:
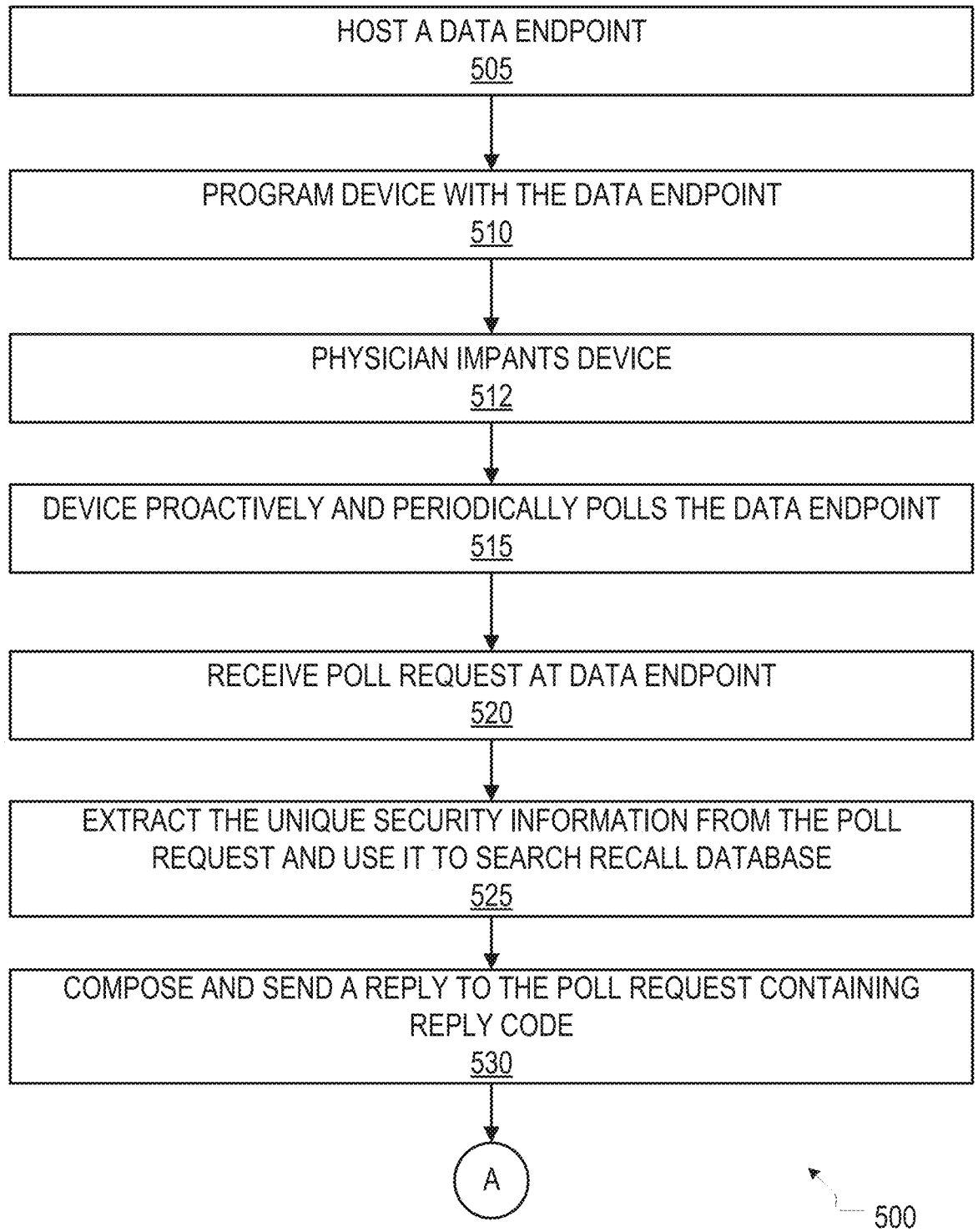
FIGS. 5A-5B are a flow chart illustrating one method of operating the reverse recall system of FIG. 4, consistent with some embodiments.
Figure 5B:
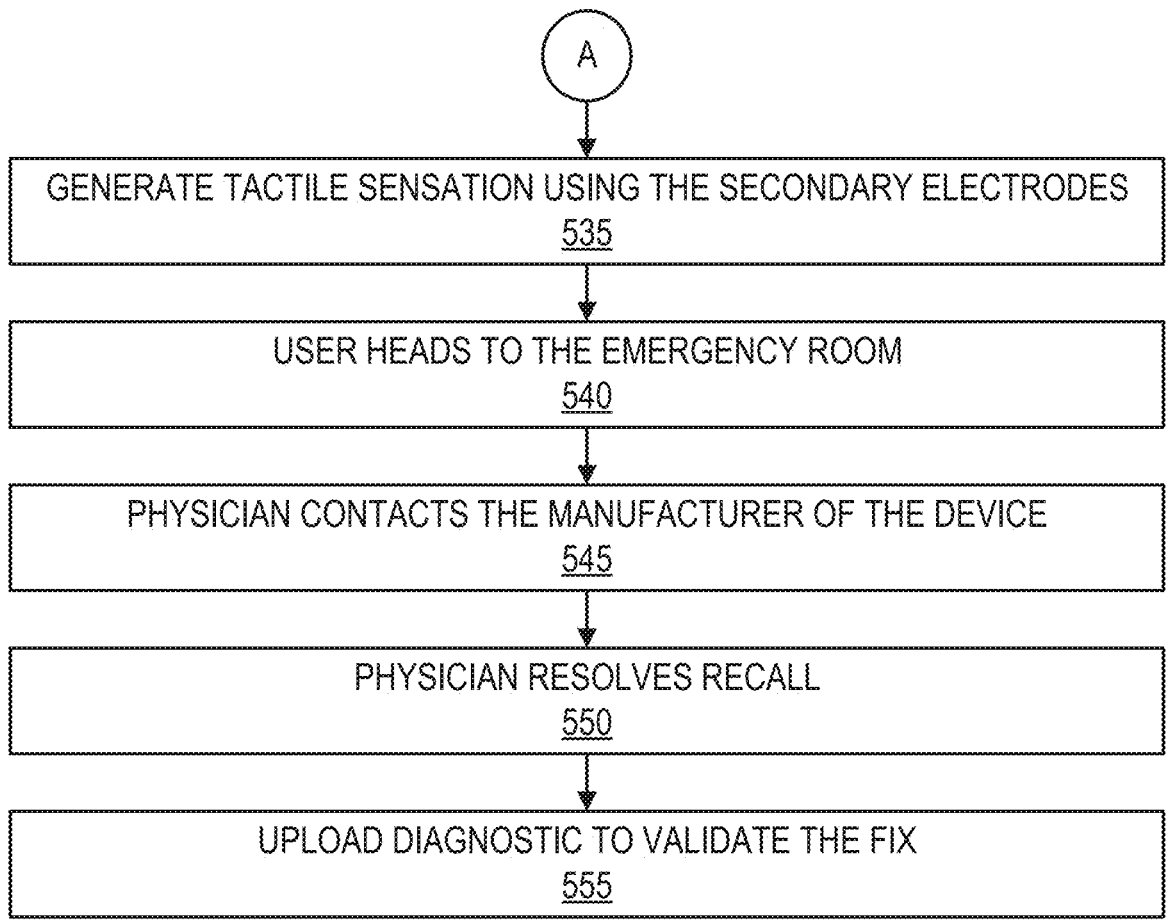

FIGS. 5A-5B are a flow chart illustrating one method of operating 500 the reverse recall system 400 of FIG. 4, consistent with some embodiments. At operation 505, the device manufacturer and/or third party service provider may host a data endpoint 470, such as a REST endpoint, on the Internet at a particular address 460. This address 460 may be fixed/unchangeable for the life expectancy of the device 405 and/or its user. The data endpoint 470 may respond to poll requests with customized information about recalls on that a specific implanted device 405. The endpoint 470 may reply to the poll request in a very narrow and detailed manner, e.g., where very specific info, like serial number of the device, or date of manufacture, mode number, etc., can allow the implanted device 105 to definitively determine whether or not there is a recall on it. Additionally or alternatively, the endpoint 470 may encrypt and/or sign the reply so that any tampering of the reply en route will be immediately apparent.

At operation 510, the device 405 may be programmed with the data endpoint 470, and optionally the manufacturer's public key, into the device 405 at the factory by the device manufacturer. The device 405, in turn, knows that it may poll this endpoint 470 to determine whether or not a recall created has been issued. At operation 512, the device 405 may be implanted in a patient by their physician.

After the implanted device 405 has been implanted, the device 405 may begin to proactively and periodically poll the manufacturer's data endpoint 470 via its wireless network interface 435 at operation 515, e.g., every few minutes, every hour, every day, etc. The poll request may include information that uniquely identifies the implanted device 405 (e.g., with the serial number 458), and may request a response code indicating whether or not any recalls have been issued for it (i.e., for that specific implanted device 405). If there is no internet connectivity, the polling job may be paused, then may resume immediately when connectivity is regained. Some embodiments may also protect this request using one or more of a variety of security systems to prevent tampering. For example, for REST endpoints 470, some embodiments may use TLS encryption, SSL certificates, certificate authorities, and/or PKI digital signatures.

At operation 520, the data endpoint 470 may receive the poll request. Next, at operation 525, the manufacturer may extract the unique security information from the request and use it to search a database 499 of recalls to determine whether or not any recalls have been issued for the requesting device. At operation 530, the manufacturer may compose and send a reply to the poll request. This reply request may include a code indicating the presence or absence of a recall and may sign the recall code so that the device 405 may be assured that the reply message was not tampered with en route. Additionally or alternatively, some embodiments may also protect this reply message using, e.g., TLS encryption, SSL certificates, certificate authorities, and/or PKI digital signatures.

If the reply indicates that there is a recall, implanted medical device 405 may generate a tactile sensation using the secondary electrodes 440 at operation 535. This tactile sensation may produce provide feedback (e.g., mild discomfort) directly to the user to seek medical attention, e.g., because something is wrong with that specific implanted medical device 405. This tactile sensation may be localized, e.g., in the vicinity of the implanted device, so the patient knows that the implanted medical device 405 is its cause. In this way, the tactile sensation may act as instinctual feedback to convey to the user the urgency of the problem. That is, the user/patient may not know there is recall, but should know something is "wrong" and that needs to be checked immediately. Additionally or alternatively, some embodiments may pulse the tactile feedback in a distinctive pattern that may help the patient know that the tactile sensation is related to the implanted medical device 405.

At operation 540, the user heads to the emergency room. At operation 545, a physician in the emergency room may contact the manufacturer of the device and obtain details about the recall. Additionally or alternatively, the physician may perform a diagnostic of the implanted device 405. The issue that prompted the recall on the device may be resolved by the physician, and then the patient can now safely go home at operation 550 (e.g., medical device battery replacement, or the like).

Optionally, a diagnostic to validate the fix may be uploaded to the device 405 at operation 555 as part of procedure performed in emergency room. In these embodiments, now that the issue has been safely resolved, the implanted device 405 may notify the device manufacturer via the data endpoint 470 that this specific recall has been completed on this specific implanted device 405. As a result, the device manufacturer may now know which recalled devices 405 have been corrected, and thus also has up-to-date information on which specific devices 405 do not need additional notifications.

Figure 6:
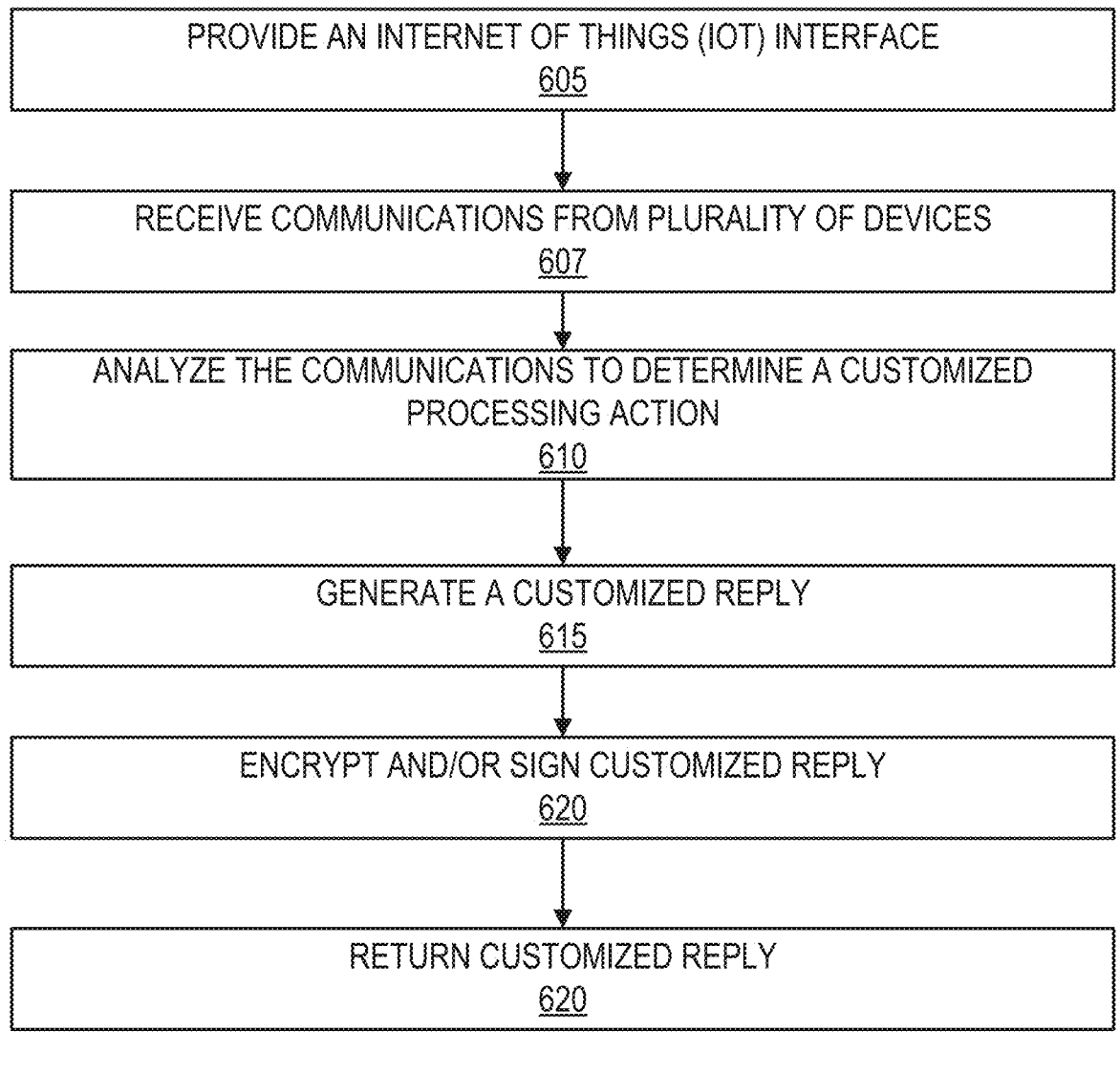
FIG. 6 is a flow chart illustrating one method for communicating an action to be performed by a device by a manufacturer of that device, consistent with some embodiments.

FIG. 6 is a flow chart illustrating one method for communicating an action to be performed by a device by a manufacturer of that device, consistent with some embodiments. At operation 605, the manufacturer may provide an Internet of things (IoT) interface, such as endpoint 460, for communicating with a plurality of devices, such as implanted devices 405. This IoT interface may be provided by a DPS 100 or cloud service 50 operated by the manufacturer or by a recall service that manages recalls for a plurality of manufacturers. Next, the manufacturer and/or recall service may receive, by the IoT interface, communications from the plurality of devices at operation 607. These communications may comprise periodic poll requests seeking recall status information, and may comprise device identification information, such as serial number 458, from the plurality of devices.

At operation 610, the manufacturer and/or recall service may analyze the communications from the plurality of devices to determine a customized processing action for each of the plurality of devices. This may include a recall module 498 querying a database 499 for customized recall information for the device associated with the identification information. At operation 615, the manufacturer and/or recall service may generate a customized reply, such as reply 485. This customized reply may contain a feedback action (e.g., to generate a tactile sensation to a user of the device 405) to be performed by the device. The customized reply may further contain an intensity level for the feedback action. Alternatively, the customized reply may indicate that no action by the device is necessary. The customized reply may be encrypted and/or signed by the manufacturer and/or recall service at operation 620 and then returned, by the IoT interface to the devices, at operation 625.

Figure 7:
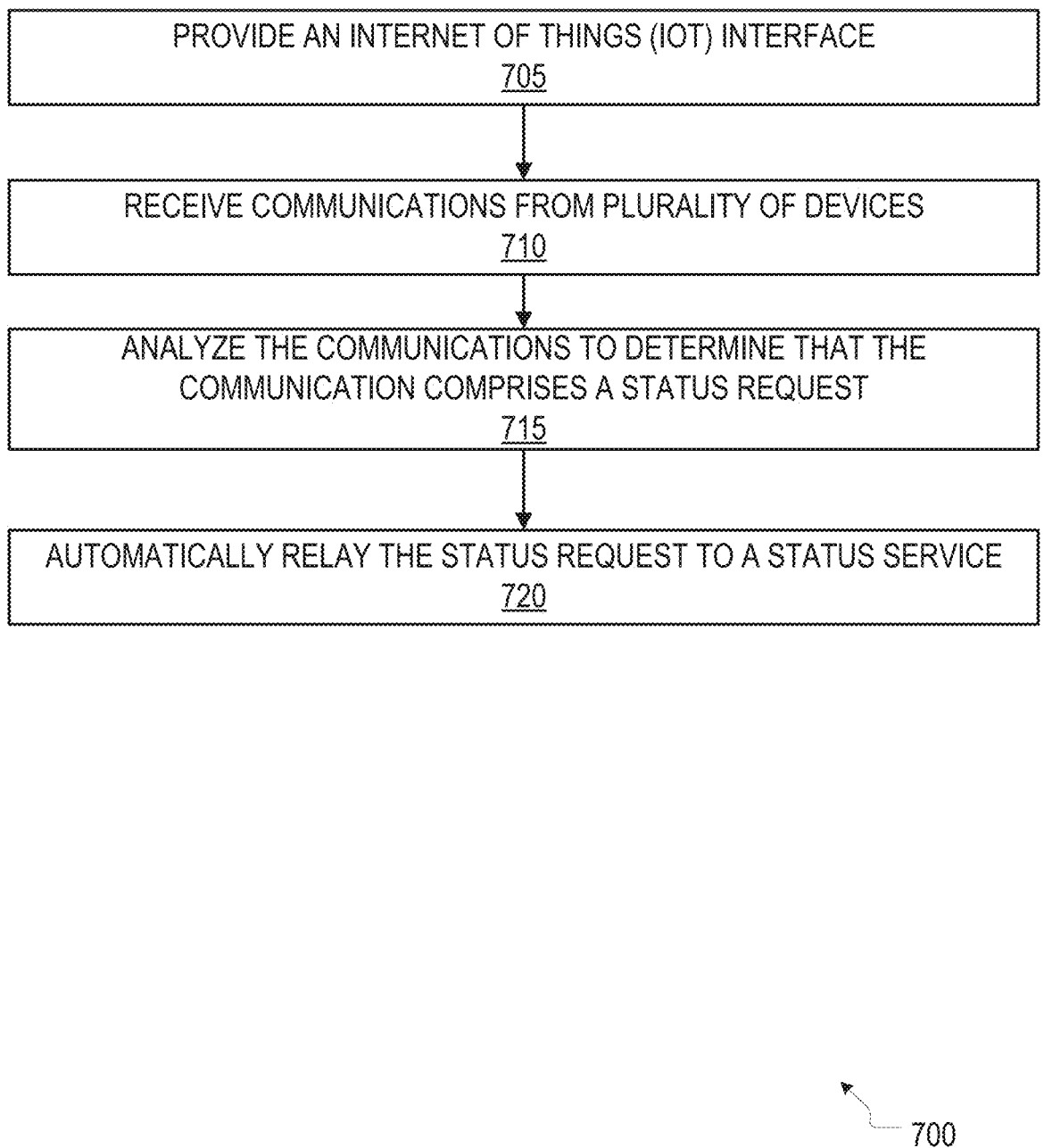
FIG. 7 is a flow chart illustrating one method of operating a relay service by a network device, such as a smartphone or cellular base station, consistent with some embodiments.

FIG. 7 is a flow chart illustrating one method of operating a relay service by a network device, such as a smartphone or cellular base station, consistent with some embodiments. At operation 705, the network device may provide an Internet of things (IoT) interface for communicating with a plurality of devices, such as implanted devices 405. The network device may then receive, by the IoT interface, a communication from one of the plurality of devices at operation 710. In response, the network device may determine, by a processor, that the communication comprises a status request at operation 715. In some embodiments, this determination may be based on the communication being sent on a predetermined network port or may be based on the presence of a predetermined handshake prefix code. The network device may then automatically relay the status request to a status service at operation 720. The status request may comprise a poll request from an implanted medical device 405 requesting information about recalls.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

Therefore, it is desired that the embodiments described herein be considered in all respects as illustrative, not restrictive, and that reference be made to the appended claims for determining the scope of the invention.

What is claimed is:

1. A recall notification method, comprising:
periodically transmitting, by a network interface of a medical device implanted in a user's body, a poll request to a recall service endpoint at a fixed address;
extracting, by the recall service endpoint, unique security information from the poll request;
determining, by the recall service endpoint, whether or not any recalls have been issued for the medical device;
receiving, by the network interface of the medical device in response to the poll request, a recall notification from the recall service endpoint;
in response to receiving the recall notification, directly notifying the user, wherein directly notifying comprises generating a tactile sensation in the user's body via a secondary electrode of the medical device;
in response to generating the tactile sensation, allowing the user to switch off the tactile sensation, wherein an intensity of the tactile sensation is related to a severity level associated with the recall notification; and
in response to directly notifying the user, causing the user to have the medical device checked.

2. The method of claim 1, wherein the poll request comprises a serial number for the medical device; and wherein the serial number is used to customize the recall notification for the medical device.

3. The method of claim 1, wherein the recall notification is signed by a manufacturer of the medical device.

4. The method of claim 1, wherein:
the medical device comprises a nonvolatile memory unit; and
wherein the poll request is directed to an Internet address stored in the nonvolatile memory unit before implantation in the user's body.

5. A notification method for an implanted medical device, comprising:
detecting, by a processor of the implanted medical device and in response to a poll request to a recall service endpoint at a fixed address, a service condition; and
extracting, by the recall service endpoint, unique security information from the poll request;
determining, by the recall service endpoint, whether or not any recalls have been issued for the implanted medical device;
in response to the service condition, generating a notification comprising a tactile sensation in a user's body, wherein the generating comprises producing the tactile sensation via a secondary electrode of the implanted medical device;

in response to generating the notification of the tactile sensation, allowing the user to switch off the tactile sensation, wherein an intensity of the tactile sensation is related to a severity level associated with the service condition; and in response to generating the notification, causing the user to have the implanted medical device checked.

6. The method of claim 5, wherein the detecting comprises:

periodically transmitting, by a network interface of the implanted medical device, the poll request to the recall service endpoint; and receiving, by the network interface in response to the poll request, a service notification.

7. The method of claim 6, wherein the poll request comprises a serial number for the implanted medical device; and wherein the serial number is used to customize the service notification for the implanted medical device.

8. The method of claim 6, further comprising receiving, from a nonvolatile memory unit of the implanted medical, an internet address for the recall service endpoint, wherein the internet address was stored in the nonvolatile memory unit before implantation in the user's body.

9. The method of claim 6, wherein the service condition is a recall of the implanted medical device.

* * * * *